(12) United States Patent
Osada et al.

(10) Patent No.: US 9,709,523 B1
(45) Date of Patent: Jul. 18, 2017

(54) GAS DETECTION APPARATUS

(71) Applicant: KABUSHIKI KAISHA TOSHIBA, Minato-ku (JP)

(72) Inventors: Norikazu Osada, Meguro (JP); Hirohisa Miyamoto, Kamakura (JP); Ko Yamada, Yokohama (JP); Hiroko Nakamura, Yokohama (JP); Mitsuhiro Oki, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/259,587

(22) Filed: Sep. 8, 2016

(30) Foreign Application Priority Data

Mar. 16, 2016 (JP) .................. 2016-051974

(51) Int. Cl.
H01L 29/49 (2006.01)
G01N 27/414 (2006.01)

(52) U.S. Cl.
CPC ................ G01N 27/4141 (2013.01)

(58) Field of Classification Search
CPC ................ G01N 27/4141
See application file for complete search history.

(56) References Cited

U.S. PATENT DOCUMENTS

| 5,246,859 A * | 9/1993 | Nelson | G01N 31/223 |
| | | | 205/778 |
| 2004/0023428 A1* | 2/2004 | Gole | G01N 27/127 |
| | | | 438/48 |
| 2005/0129573 A1 | 6/2005 | Gabriel et al. | |
| 2010/0086439 A1 | 4/2010 | Yamanaka et al. | |
| 2013/0018559 A1 | 1/2013 | Epple et al. | |
| 2013/0273665 A1 | 10/2013 | Swager et al. | |

FOREIGN PATENT DOCUMENTS

| JP | 2004-515782 | 5/2004 |
| JP | 2007-505323 A | 3/2007 |
| JP | 2010-019688 | 1/2010 |
| JP | 2010-139269 | 6/2010 |
| JP | 2012-247189 | 12/2012 |

(Continued)

OTHER PUBLICATIONS

Xinran Wang et al. "N-Doping of Graphene Through Electrothermal Reactions with Ammonia" Science vol. 324, May 8, 2009, pp. 768-771.

Primary Examiner — Michael Shingleton
(74) Attorney, Agent, or Firm — Oblon, McClelland, Maier & Neustadt, L.L.P.

(57) ABSTRACT

A gas detection apparatus according to an embodiment includes: a collection unit collecting a detection target gas containing a gas molecule to be detected; a detector including a plurality of detection cells each including a sensor unit and an organic probe disposed at the sensor unit, the organic probe capturing the gas molecule collected by the collection unit; a discriminator discriminating the gas molecule by a signal pattern based on an intensity difference of detection signals generated with the gas molecule being captured by the organic probes of the plurality of detection cells; and a reactivation unit applying heat to the organic probe which has the captured gas molecule to be desorbed the gas molecule from the organic probe.

9 Claims, 5 Drawing Sheets

(56) References Cited

FOREIGN PATENT DOCUMENTS

| | | |
|---|---|---|
| JP | 2014-227304 | 12/2014 |
| JP | 2015-515622 | 5/2015 |
| WO | WO 02/48701 A2 | 6/2002 |
| WO | WO 2007/108122 A1 | 9/2007 |
| WO | WO 2008/108371 A1 | 9/2008 |

* cited by examiner

GAS DETECTION APPARATUS

CROSS REFERENCE TO RELATED APPLICATION

This application is based upon and claims the benefit of priority from Japanese Patent Application No. 2016-051974, filed on Mar. 16, 2016; the entire contents of which are incorporated herein by reference.

FIELD

Embodiments described herein relate generally to a gas detection apparatus.

BACKGROUND

Recent years, global environment issues due to an air pollution have emerged, and a gas detection equipment has been required to have a higher sensitivity against a background of tightened regulation of an emission gas from a factory facility or an automobile. An environmental criteria in relation to an air pollution requires, for example, $NO_x$ to be equal to or less than 40 ppb (parts per billion). Thus, an extremely small amount of gas component in the order of ppb is required to be detected. Also, apart from the environmental issues, in the field of a defense or a security, to develop an accurate and quick analytical method has been becoming a challenge ahead with respect to the NBC (nuclear: N; biological agent: B agent; chemical agent: C agent) substances. Amongst them, with regard to the C agent, as observed in the Tokyo subway sarin gas attack, it is required to quickly sense a noxious gas which has an extremely higher harm to a human body. In this regard, it is required to detect an extremely low concentration of a gas component on a real-time basis in order to prevent a secondary injury from occurring. Various methods have been known for detecting the gas component having a relatively higher concentration. In contrast, however, the detection methods are limited for detecting the gas component having a concentration of ppb (parts per billion) or ppt (parts per trillion), which corresponds to the extremely low concentration.

For example, at a disaster site or a site at which an act of terrorism occurs or the like, it is desired to sense the risk in advance by detecting the extremely small amount of the gas component. In many cases, such gas component having the extremely low concentration is detected by use of a large equipment in research facilities. In this case, a large sized installation type equipment, which is expensive and has large weight and volume, is required such as a gas chromatography or a mass spectrometer or the like. On the other hand, when direct measuring in the field is demanded, it is necessary to rely on a simplified measuring method for detecting by use of a biological reaction mechanism. Such simplified method has, however, a lot of problems of, for example, a limited storage life, temperature control, and the determination being limited to a presence or absence of the gas component. Under such circumstances, it has been demanded to provide an apparatus that is capable of detecting the gas component having an extremely low concentration on a real-time basis, in other words, an apparatus that has a smaller weight and volume and a better portability and is capable of detecting the gas component having the extremely low concentration in the order of ppt to ppb in a selective manner with higher sensitivity.

As a detection element for the gas component with low concentration, for example, a certain element has been known that has a conductive layer in which a surface of a carbon nanostructure is surface modified with an organic substance or the like capable of selectively reacting or adsorbing with a specific substance and measures a potential difference or the like which varies depending on the gas component adhered to the surface of the carbon nanostructure. In this type of detection element, for example, when a similar component or the like to the detection target gas component is immixed as an impurity in a gas obtained in air, it is likely to fail to accurately detect the detection target gas component. Furthermore, when the organic substance which functions as a detection probe strongly adsorbs the detection target gas component, after then it becomes impossible to detect the gas component again. In other words, it becomes impossible to use the detection element in a repetitive manner. For this reason, it is demanded to provide an apparatus that is capable of repetitively detecting the gas component having the extremely low concentration in a selective manner with higher sensitivity.

DETAILED DESCRIPTION

Figure 1:
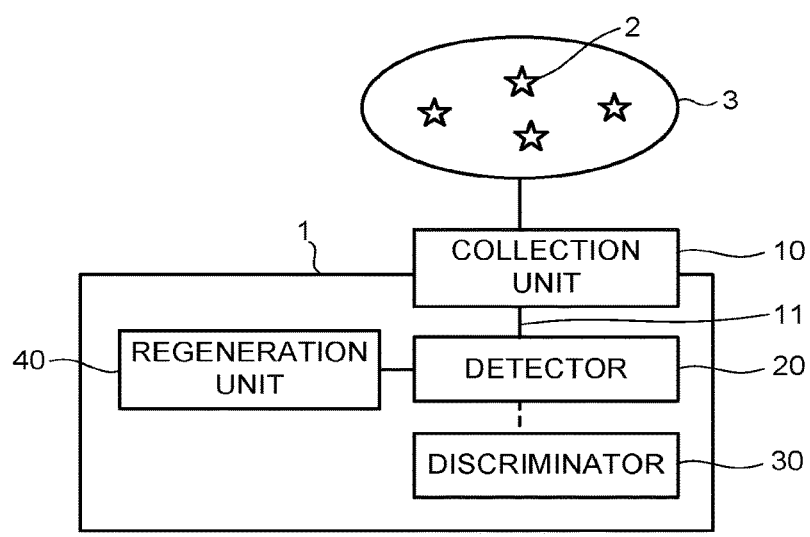
FIG. 1 is a block diagram illustrating a gas detection apparatus according to an embodiment.

According to an embodiment, a gas detection apparatus is provided. The gas detection apparatus includes: a collection unit collecting detection target gas containing gas molecules to be detected; a detector including a plurality of detection cells each having a sensor unit and an organic probe disposed at the sensor unit, the organic probe capturing the gas molecules collected by the collection unit; a discriminator discriminating the gas molecules by a signal pattern based on an intensity difference of detection signals generated with the gas molecules being captured by the organic probes of the plurality of detection cells; and a reactivation unit applying heat to the organic probes which have the captured gas molecules to be desorbed the gas molecules from the organic probes.

Hereinafter, a gas detection apparatus and a method for detecting a gas according to embodiments will now be described with reference to the accompanying drawings. In the embodiments, like or same reference numerals designate corresponding or identical configurations, and therefore such configurations may not be described repetitively. The drawings are schematically illustrated. For example, the relationship between a thickness and plane dimensions, a ratio of thicknesses of respective units and the like may differ from actual dimensions.

FIG. 1 is a block diagram illustrating a gas detection apparatus according to a first embodiment. The gas detection apparatus 1 shown in FIG. 1 is an apparatus that detects a to-be-detected gas molecule 2 from a detection target gas 3 containing, for example, to-be-detected gas molecules (to-be-detected substances) generated from a gas generation source. The gas detection apparatus 1 includes a collection unit 10, a detector 20 and a discriminator 30. The detector 20 has a reactivation unit 40. The detection target gas 3 containing the to-be-detected gas molecules 2 is, first, collected by the collection unit 10 of the gas detection apparatus 1. The collection unit 10 has a collection port for the detection target gas 3 and is connected to the detector 20 through a gas flow channel 11. The collection unit 10 may include a filer or the like for eliminating an impurity contained in the detection target gas 3.

In some cases, the detection target gas 3 contains, as an impurity, a substance that has a molecular weight or a molecular structure or the like similar to the to-be-detected gas molecule 2. Also, in many cases, the to-be-detected gas molecule 2 drifting in the air exists in a state that the to-be-detected gas molecule 2 is immixed with various contaminants such as an odorous component or a fine particle or the like. From those perspectives, the detection target gas 3 may be sent to the gas detection apparatus 1 after the detection target gas 3 is preprocessed by a filer device, an absorbing tube, or a molecular distribution device or the like in advance. For the filer device, generally-used moderate high performance filter or the like is used. For the molecular distribution device, an apparatus can be used that ionizes the detection target gas 3 to allow the detection target gas 3 to form an ionized substance group, applies voltage to the ionized substance group to allow the ionized substance group to fly at a speed proportional to the mass thereof, and separates an ionized substance of the to-be-detected gas molecule 2 from the ionized substance group using a flight speed based on the mass difference among ionized substances and a time-of-flight thereof.

Figure 2:
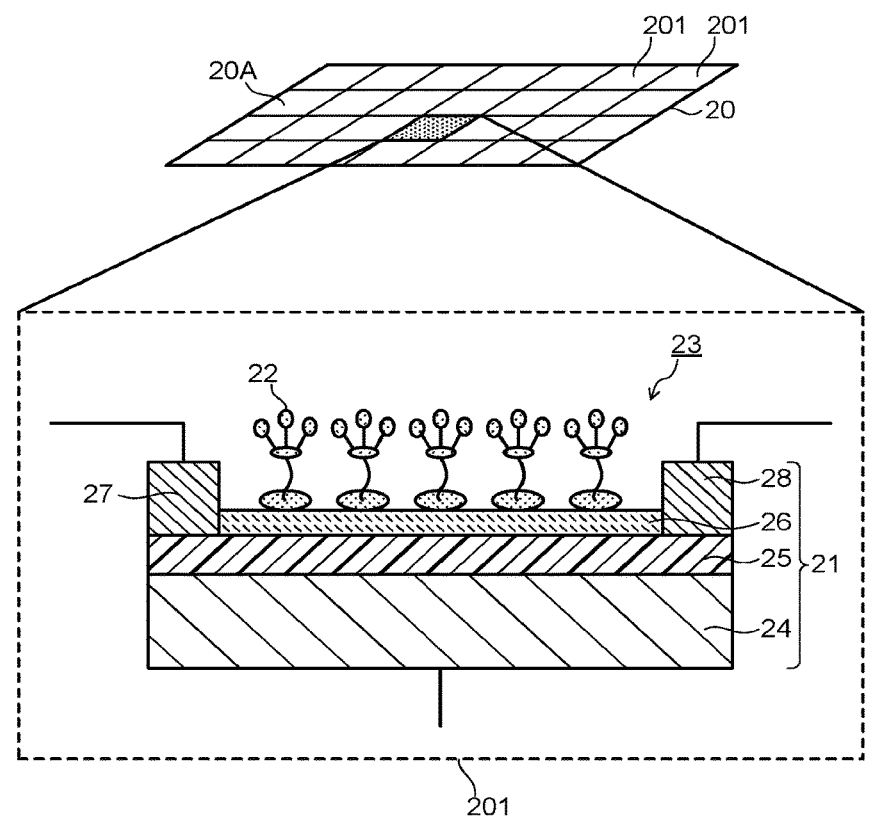
FIG. 2 is a view illustrating an exemplary configuration of a detector of the gas detection apparatus according to the embodiment.

The detection target gas 3 containing the to-be-detected gas molecules 2 is collected by the collection unit 10 directly, or alternatively after the detection target gas 3 is preprocessed by a device such as the filter device or the molecular distribution device or the like. The to-be-detected gas molecules 2 collected by the collection unit 10 are then sent to the detector 20 thorough the gas flow channel 11. The detector 20 includes, as shown in FIG. 2, a detection surface 20A which is partitioned into a plurality of detection cells 201. Each of the plurality of detection cells 201 includes a detection element 23 having a sensor unit 21 and an organic probe 22 disposed at the sensor unit 21. FIG. 2 illustrates the detection element 23 in which the graphene field effect transistor (GFET) is used for the sensor unit 21.

The GFET serving as the sensor unit 21 includes a semiconductor substrate 24 which functions as a gate electrode, an insulating film 25 provided as a gate insulating layer on the semiconductor substrate 24, a graphene layer 26 provided as a channel on the insulating film 25, a source electrode 27 provided at one end of the graphene layer 26, and a drain electrode 28 provided at the other end of the graphene layer 26 to form a back gate type FET sensor structure. The organic probe 22 is provided on the graphene layer 26 of the GFET 21. The to-be-detected gas molecules 2 guided into the detector 20 are captured by the organic probe 22 on the graphene layer 26. With electrons being moved from the to-be-detected gas molecules 2 captured by the organic probe 22 to the GFET 31, the electrical detection is carried out. In this way, an intended to-be-detected gas molecule 2 is detected in a selective manner.

An organic substance constituting the organic probe 22 has a dissolvable property in solvent. Thus, it is possible to arrange the organic probe 22 on the graphene layer 26 by applying on the graphene layer 26 solution in which the organic substance is dissolved. In order to facilitate to achieve an interaction with the graphene, the organic probe 22 has preferably a portion having a certain structure such as a pyrene ring. The molecule having the structure such as the pyrene ring interacts with a hexagonally shaped π electron system constituted with carbon of the graphene to form an interaction state of so-called π-π stacking. The π-π stacking is formed between the pyrene ring and the graphene by dissolving probe molecules with low concentration in the solvent and applying the solvent on the graphene, and the probe molecules are aligned and fixed on the graphene 26. By use of this kind of the self-alignment action, it is possible to arrange the organic probe 22 on the graphene layer 26.

When the to-be-detected gas molecule 2 is captured (adsorbed) by the organic probe 22 provided on the graphene layer 26, an output from the GFET31 changes. When the graphene has a one layer, as it means the zero-gap, normally between the source electrode 27 and the drain electrode 28 continues to be electrified. On the other hand, when a number of graphene layers increases to two or three layers, although the bang gap is generated, such band gap in an actual system is relatively smaller than those considered from the strict theoretical value. When the gate insulating layer 25 has the dielectric constant approximately similar to the silicon dioxide film, in many cases between the source electrode 27 and the drain electrode 28 continues to be electrified. The graphene layer 26 is not limited to the single layer structure of the graphene, but alternatively may be constituted with a laminated body having approximately equal to or less than five layers. The graphene layer 26 is formed by, for example, a transcription onto the substrate by peeling off method from the graphite. Alternatively, the graphene layer 26 is formed by the transcription onto the substrate after being deposited onto a surface of metal by use of the chemical vapor deposition (CVD) method.

The to-be-detected gas molecule 2 flying in the vicinity of the organic probe 22 is attracted to the organic probe 22 by the force of hydrogen bond or the like, and in some cases, contacts the organic probe 22. When the contact of the to-be-detected gas molecule 2 occurs, then an interchange of electrons occurs with the organic probe 22, and an electrical change is transmitted to the graphene layer 26 contacting the organic probe 22. The electrical change transmitted from the organic probe 22 to the graphene layer 26 disturbs the flow of electricity between the source electrode 27 and the drain electrode 28 so that the GFET 21 functions as a sensor. With the GFET 21 using the graphene layer 26 as a channel being employed, even an extremely slight electric change appears significantly as an output. As a result, it is possible to constitute the detection element 23 with higher sensitivity.

The sensor using the GFET 21 also has a tendency to electrify between the source electrode 27 and the drain electrode 28 without applying voltage to the gate electrode 24, because the graphene has a property as the zero-gap semiconductor. Thus, such sensor can function as it is. Nevertheless, normally between the source electrode 27 and the drain electrode 28 is electrified in a state that the voltage is applied to the gate electrode 24, and the electric change of the gate electrode 24 is observed when the organic probe 22 has captured the to-be-detected gas molecule 2. The detector 20 includes a circuit that is capable of arbitrarily controlling the back gate voltage or the voltage and the current between the source electrode 27 and the drain electrode 28. The detector 20 includes a circuit or a detector that is capable of detecting the voltage and the current thereof.

In the above mentioned detection of the to-be-detected gas molecule 2 by the detection element 23, as the travelling of the electron is higher to the GFET 31 from the to-be-detected gas molecule 2 captured by the organic probe 22, the function as the sensor becomes higher. The sensor using the GFET 21 is considered to be the FET sensor with the highest sensitivity, and can improve the sensitivity approximately three times compared to a sensor using the carbon nanotube. As a result, it is possible to detect the to-be-detected gas molecule 2 with higher sensitivity by using the detection element 23 that combines the GFET 21 with the organic probe 22.

FIG. 2 illustrates a detection surface 20A on which the detection cells 201 are arranged in a grid shape (array shape). It however does not mean to limit the present embodiment. A plurality of detection cells 201 may be linearly arranged. Among the organic probes 22 respectively provided on the graphene layers 26 of the plurality of detection units 201, at least a part of organic probes 22 have a different binding strength with the to-be-detected gas molecules 2 one another. In other words, the plurality of detection cells 201 include a plurality of organic probes 22 that have different binding strength with the to-be-detected gas molecule 2 one another. All of the organic probes 22 may have different binding strengths with the to-be-detected gas molecule 2 one another. Alternatively, a part of the organic probes 22 may have a different binding strength with the to-be-detected gas molecule 2 one another. Yet alternatively, in place of the organic probes 22 that have different binging strengths with the to-be-detected gas molecule 2 one another, the density of the organic probes 22 may be changed on the graphene layers 26.

Figure 3:
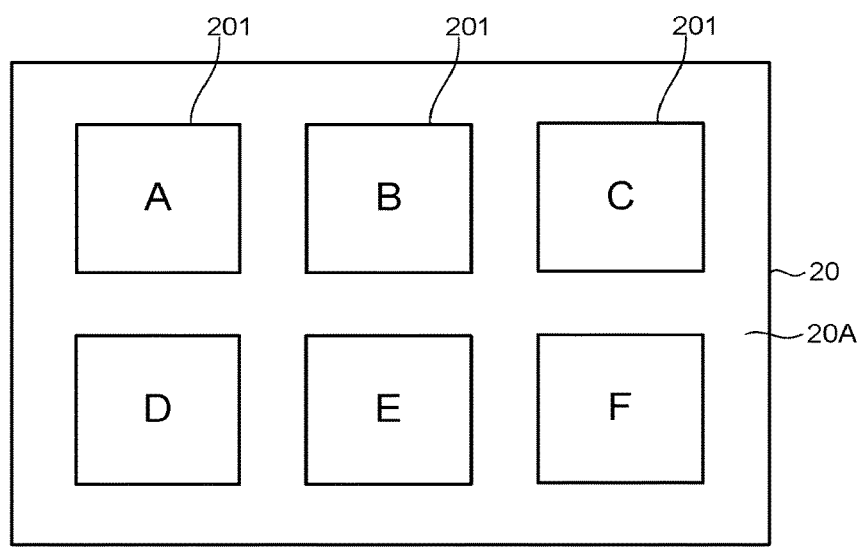
FIG. 3 is a view illustrating an example of a plurality of detection cells of the gas detection apparatus according to the embodiment.
Figure 4:
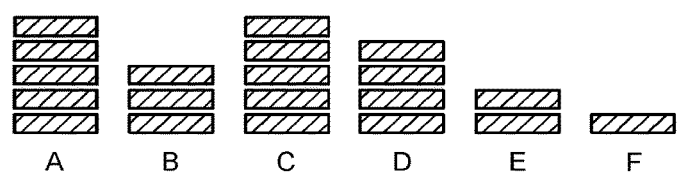
FIG. 4 is a view illustrating an example of a detection result of the to-be-detected gas molecule by the plurality of detection cells shown in FIG. 3.

FIG. 3 illustrates a sensor having a grid shape in which the detection surface 20A of the detector 20 is partitioned into six detection cells 201, that is, a detection cell A, a detection cell B, a detection cell C, a detection cell D, a detection cell E, and a detection cell F. Out of the detection cells A to F, the different types of organic probes 22, in other words, a plurality of organic probes 22 having the different binding strengths with the to-be-detected gas molecule 2 one another, are provided for at least a part of detection cells. The plurality of organic probes 22 interact with the to-be-detected gas molecules 2, respectively, and have different signal intensity of the detection signals one another, respectively, as they have different acting strength (binding strength) with the to-be-detected gas molecule 2. FIG. 4 illustrates an example of the detection signals detected by the detection cells A to F, respectively. The detection signals from the detection cells A to F have, as shown in FIG. 4, different signal intensities one another based on the binding strengths of the organic probes 22 with the to-be-detected gas molecule 2.

As the organic probe 22 provided on the graphene layer 26, an organic compound having a hydroxy group (—OH) or an amino group (—NH$_2$) as a reactive group is used. However, it should be noted that, when this kind of reactive group is solely used, the reactive group hardly reacts with the gas component. In order to enhance the hydrogen bonding property, an organic compound in which a functional group (neighboring group) having an excellent inductive effect is introduced into a neighboring portion of the reactive group is used. As the neighboring group to the hydroxy group (—OH) as the reactive group, an alkyl group displaced with a fluorine atom such as trifluoromethyl group (—CF$_3$) or hexafluoroethyl group (—C$_2$F$_5$) or the like, a functional group containing nitrogen such as a cyano group (—CN), a nitro group (—NO$_2$), or a —CHN group or the like, or an alkyl group such as a methyl group (—CH$_3$) or an ethyl group (—C$_2$H$_5$) or the like may be used. As the neighboring group to the amino group (—NH$_2$) as the reactive group, an ether linking group (—O—) may be used.

The organic probe 22 is preferably constituted with an organic compound having a head portion HS, which has a reactive group such as the hydroxy group or the amino group or the like and the above mentioned neighboring group, a base portion BS, which serves as an installation portion for the graphene layer 26, and a connecting portion CS, which connects the head portion HS to the base portion BS. The head portion HS is preferably a monovalent aromatic hydrocarbon group having the reactive group and the neighboring group, and more preferably a phenyl group having an alkyl group in which the reactive group and the neighboring group are bound to the same carbon (carbon number: approximately 1 to 5).

The base portion BS is preferably a monovalent substituted or unsubstituted polycyclic aromatic hydrocarbon group having a polycyclic structure such as a pyrene ring, an anthracene ring, a naphthacene ring, or a phenanthrene ring or the like, and more preferably a substituted or unsubstituted pyrene group. The connecting portion CS may be a bivalent group. The connecting portion CS may be an alkylene group such as a methylene group or an ethylene group or the like. The connecting portion CS has preferably an ether bond (—O—), an ester bond (—C(=O)O—), a carbonyl bond (—CO—), an amide bond (—NH—CO—), an imide bond (—CO—NH—CO—) or the like, and more preferably has the amide bond.

In the organic compound constituting the above mentioned organic probe 22, the binding strength with the to-be-detected gas molecule 2 can be regulated depending on the type of reactive group, the type or the number or the like of the neighboring group to the reactive group. For example, when comparing an organic compound having a CH$_3$ group as the neighboring group and an organic compound having a CF$_3$ group as the neighboring group, the trifluoromethyl group achieves an effect to enhance an activity of the reactive group (OH group) with fluorine having a higher electronegative degree, while the methyl group has less such effect. In light of the above observation, it is possible to obtain the different binding strengths with the to-be-detected gas molecule 2 one another. Also, when the number of the CF$_3$ group or the like is different as the neighboring group, it is possible to obtain the different binding strengths with the to-be-detected gas molecule 2 one another. Yet furthermore, also, when the type of functional group containing the reactive group is different, still it is possible to obtain the different binding strengths with the to-be-detected gas molecule 2 one another.

As described above, it is possible to regulate the binding strength with the to-be-detected gas molecule 2 depending on the type of the organic compound constituting the organic probe 22. Also, it is possible to regulate the binding strength with the to-be-detected gas molecule 2 by regulating the density of the organic probes 22 provided in the detection cell 201. The signal intensity of the detection signals from the detection cells A to F differs one another based on the difference in the binding strength with the to-be-detected gas molecule 2 of the organic probe 22.

The signals detected by the detection cells A to F are sent to a discriminator 30 and undergoes the signal processing. The discriminator 30 transforms the detection signals from the detection cells A to F into intensities, and analyzes a signal pattern based on the difference in the intensities of those detection signals (for example, pattern of six detection signals shown in FIG. 4). The discriminator 30 stores a signal pattern corresponding to a to-be-detected substance. Thus, the discriminator 30 discriminates the to-be-detected gas molecule 2 detected by the detector 20 by comparing the stored signal pattern and a signal pattern detected by the detection cells A to F. This type of signal processing method is referred to as a pattern recognition method. According to the pattern recognition method, it is possible to detect and discriminate the to-be-detected gas molecule 2 with the signal pattern specific to the to-be-detected substance as, for example, a fingerprint inspection. As a result, it is possible to detect a gas component with the extremely low concentration in the order of ppt to ppb (to-be-detected gas molecule 2) in a selective manner with higher sensitivity.

By applying the above mentioned pattern recognition method, even in the case that an impurity is immixed into the detection target gas to be introduced into the detector 20, still it is possible to detect and discriminate the to-be-detected gas molecule 2 in a selective manner with higher sensitivity. For example, in the case that the to-be-detected gas molecule 2 is dimethyl methylphosphonic acid (DMMP, the molecule weight: 124), which is a typical material for a noxious organic phosphorous compound, there are an agricultural chemical containing phosphoric acid such as dichlorvos having a similar chemical structure and an organic phosphorous pesticide with a lot of usage examples such as malathion, chlorpyrifos, or diazinon or the like. In order to prevent an erroneous detection of those substances from occurring, it is effective to discriminate with the signal patterns as shown in FIG. 4. In other words, because the signal patterns detected by the detection cells A to F differ one another depending on the above mentioned respective substances, it is possible to detect the detection target substance in a selective manner with higher sensitivity by applying the pattern recognition method even when an impurity is immixed that has a close molecule weight and a similar constituent element.

With the to-be-detected gas molecule 2 being captured by the above mentioned organic probe 22, when the to-be-detected gas molecule 2 is discriminated, the organic probe 22 becomes a state in which the organic probe 22 has adsorbed the to-be-detected gas molecule 2. The organic probe 22 in this state can no more capture the to-be-detected gas molecule 2 so that the organic probe 22 cannot detect the to-be-detected gas molecule 2 again. As the adsorptive power by the organic probe 2 with the to-be-detected gas molecule 2 is stronger, the to-be-detected gas molecule 2 is more likely to be difficult to desorb from the organic probe 22. The organic probe 22 is required to undergo the reactivation processing. For this reason, the gas detection apparatus 1 according to the embodiment regenerates the organic probe 22 after the to-be-detected gas molecule 2 is captured (adsorbed) and then discriminated.

Figure 5:
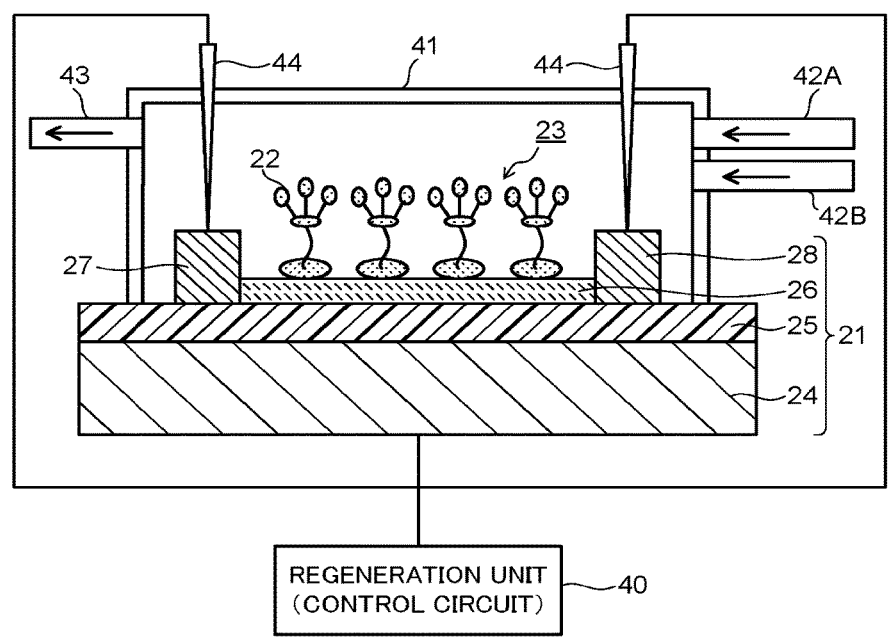
FIG. 5 is a view illustrating an exemplary configuration of the detection cells of the detector shown in FIG. 2.

As described above, the detector 20 includes a reactivation unit 40. When the reactivation processing (refreshing processing) of the organic probe 22 is carried out by the reactivation unit 40, it is preferable that a detection element 23 including the GFET 21 and the organic probe 22 of the detection cell 201 is covered by, as shown in FIG. 5, a chamber 41 that has a gas introducing tube 42 (42A and 42B) and a gas exhaust tube 43, and is capable of controlling an atmosphere. The chamber 41 is preferably installed such that the chamber 41 covers only a portion of the GFET 21 that has the organic probes 22. It should be noted that although FIG. 5 illustrates a state in which the chamber 41 covers one GFET 21, alternatively the chamber 41 may be arranged such that the chamber 41 covers a plurality of GFETs 21 constituting a plurality of detection cells 201, respectively.

The chamber 41 includes a first gas introducing tube 42A, into which the detection target gas 3 containing the to-be-detected gas molecule 2 is introduced, and a gas exhaust tube 43, which exhausts the gas inside the chamber 41. The first gas introducing tube 42A is provided with a filter or a valve or the like for eliminating an obstructive component as appropriate. The gas exhaust tube 43 is provided with a valve or an exhaust pump as appropriate. Furthermore, the chamber 41 preferably includes a second gas introducing tube 42B which supplies an inert gas or the like for regulating inside the chamber 41 to be at a predetermined atmosphere. With the above configuration, the gas atmosphere or the pressure is controlled inside the chamber 41. In order to achieve the conduction to the GFET 21 arranged inside the chamber 41, a probe 44 arranged from outside the chamber 41 is connected to the electrodes 27 and 28 of the GFET 21.

The reactivation unit 40 includes a control circuit which applies the voltage or the current between the source electrode 27 and the drain electrode 28 of the GFET 21. The control circuit is configured such that the control circuit is, for example, capable of switching between a gas sensing process among the source electrode 27, the drain electrode 28 and the gate electrode 24 of the GFET 21 and a reactivation process of the organic probe 22 by applying the voltage or the current between the source electrode 27 and the drain electrode 28. When a plurality of detection cells 201 are arranged on the detection surface 20A, the Joule heat is generated in the graphene layer 26 existing between the source electrode 27 and the drain electrode 28 by performing the voltage application or the electrification between the source electrode 27 and the drain electrode 28 for each of the cells. Furthermore, the to-be-detected gas molecule 2 adsorbed by the organic probe 22 is then desorbed by heating the organic probe 22 provided on the graphene layer 26 with the heat generated in the graphene 26. Preferably, the voltage or the current applied between the electrodes 27 and 28 is set depending on the organic probes 22 owned by each of the cells and the adsorption power or the like of the organic probes 22 with the to-be-detected gas molecule 2.

Figure 6:
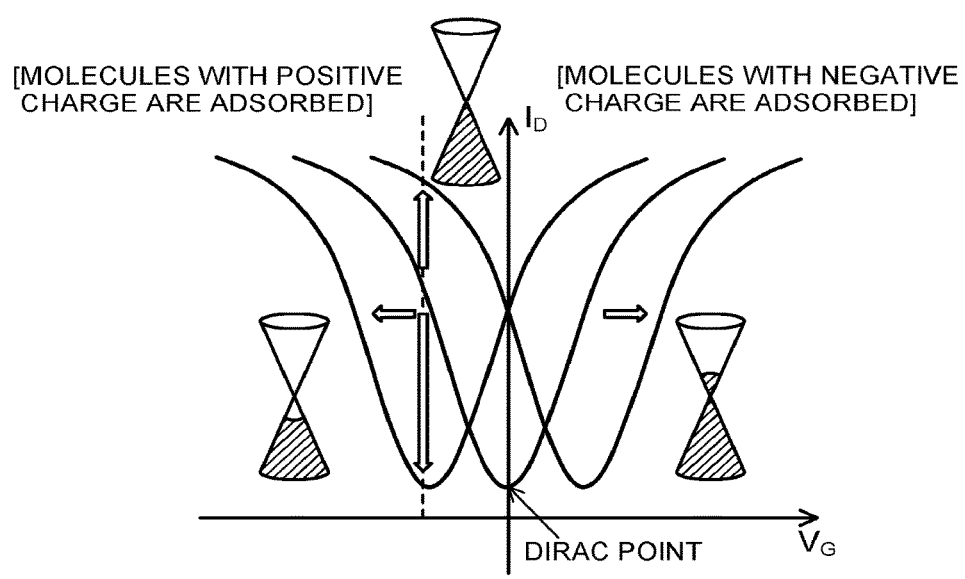
FIG. 6 is a view useful to describe a drain current used for determining an adsorption and desorption of the to-be-detected gas molecule by an organic probe of the gas detection apparatus according to the embodiment.

The gas sensing property is determined by measuring, before and after the adsorption of the to-be-detected gas molecules, the drain current when the back gate voltage is swept between −100 to +100 V under a predetermined drain voltage and a time response of the drain current under a predetermined drain voltage and a predetermined back gate voltage. In the case of graphene layer 26, when the back gate voltage is swept under a predetermined drain voltage, as shown in FIG. 6, the change in the drain current is polarized at the Dirac point. The drain current value at the Dirac point varies in association with the change in the electron state of the graphene layer 26 due to the adsorption of the gas molecule. For this reason, it is possible to determine the adsorption and desorption of the to-be-detected gas molecule 2 by the organic probe 22 based on the magnitude of the drain current value at the Dirac point or the drain current value under the predetermined back gate voltage.

The heating of the organic probe 22 by the reactivation unit 40 is set such that the temperature of the organic probe 22 is equal to or greater than the desorption temperature of the to-be-detected gas molecule 2 and less than the oxidation temperature or the decomposition temperature of the graphene layer 26. The desorption temperature of the to-be-detected gas molecule 2 by the organic probe 22 differs depending on the type of the organic compound constituting the organic probe 22 or the adsorption power or the like of the to-be-detected gas molecule 2. Therefore, the heating temperature of the graphene layer 26 is preferably set corresponding to each of the organic probes 22. Alternatively, the heating of the organic probe 22 may be performed by a heater or the like provided at the lower portion of the GFET 21 in place of the application of the voltage or the current between the source electrode 27 and the drain electrode 28.

The reactivation processing of the organic probe 22 is, for example, performed as described below. After the to-be-detected gas molecule 2 is captured and the to-be-detected gas molecule 2 is discriminated thereupon, first, the detection target gas 3 existing inside the chamber 41 is exhausted through the gas exhaust tube 43 and also the inert gas is introduced inside the chamber 41 through the second gas introducing tube 42B. As described above, the reactivation processing is performed by applying the heat to the organic probe 22 through the graphene layer 26. When the heat is applied to the organic probe 22, if the graphene layer 26 constituting the channel of the GFET 21 is exposed to the high temperature in the atmosphere containing oxygen, then the oxidation or the decomposition or the like of the graphene layer 26 may occur and the function thereof as the channel is likely to be impaired.

To cope with this problem, the inert gas such as nitrogen gas or argon gas or the like having the content of oxygen equal to or less than 1% by volume is introduced inside the chamber 41 through the second gas introducing tube 42B. After inside the chamber 41 becomes the inert gas atmosphere having the content of oxygen equal to or less than 1% by volume, the voltage or the current is applied between the source electrode 27 and the drain electrode 28 to generate the Joule heat in the graphene layer 26. By doing this, the organic probe 22 provided on the graphene layer 26 is heated up to the predetermined temperature. By performing this kind of heating processing of the organic probe 22, the to-be-detected gas molecule 2 adsorbed by the organic probe 22 is desorbed without impairing the function of the graphene layer 26. The to-be-detected gas molecule 2 desorbed from the organic probe 22 is exhausted through the gas exhaust tube 43 from the chamber 41. By desorbing the to-be-detected gas molecule 2 from the organic probe 22 and refreshing the organic probe 22, it is possible to perform again the detection processing and the discrimination processing of the gas component by way of capturing the to-be-detected gas molecule 2 by the organic probe 22.

In the gas detection apparatus 1 according to the embodiment, it is possible to detect the gas molecule with the extremely low concentration in the order of ppt to ppb in a selective manner with higher sensitivity by applying the pattern recognition method. In addition, it is possible to repetitively perform the detection the gas molecule by desorbing the to-be-detected gas molecule 2 adsorbed by the organic probe 22 during the reactivation processing. Also, it is possible to downsize the gas detection apparatus 1 by improving the detection sensitivity and the detection accuracy at the detector 20 and the discriminator 30. As a result, it is possible to provide the gas detection apparatus 1 that satisfies both of the portability and the detection accuracy and is repetitively usable. This kind of gas detection apparatus 1 effectively fulfills its function at various field sites such as a disaster site or a site of an act of terrorism or the like.

In the following description, specific examples and evaluation results thereof will be described.

Example 1

(Preparation of Detector)

A detection element in which the GFET and the organic probe are combined is prepared as described below. First, the graphene is formed by the CVD that flows gas containing the hydrocarbon system substance such as methane or the like onto a surface of a copper foil under the condition of approximately 1000 degrees Celsius. Subsequently, polymethyl methacrylate film is applied at 4000 rpm by the spin coat method, and the copper foil at an opposite face is etched with ammonium persulfate solution of 0.1 M so that a graphene film floating in the solution is recovered. By doing this, the graphene is transcribed at a side of polymethyl methacrylate film.

After a surface of the graphene is sufficiently cleaned, it is again transcribed onto a silicon substrate in which $SiO_2$ film is formed on its surface. Then after a superfluous polymethyl methacrylate film is removed, a resist is applied onto the graphene transcribed onto the silicon substrate to perform the patterning, and an electrode pattern is formed by an oxygen plasma. The FET structure having the source electrode and the drain electrode is formed by vapor-depositing an electrode material such that the source-drain spacing becomes 10 nm. In this way, the graphene is arranged onto the oxidized film formed on the surface of the silicon substrate so that a sensor structure having the back gate type GFET in which the graphene is sandwiched between the source electrode and the drain electrode and the gate electrode is provided at the silicon substrate side.

Furthermore, the organic probe is provided on the surface of the graphene. More particularly, the organic probe is provided by dissolving with the concentration of 10 nM in methanol solution and immersing the graphene sensor face therein for several minutes. In the Example 1, as shown in FIG. 3, six detection cells A to F are provided on the detection surface of the detector, and different organic compounds are provided for the respective cells as the organic probes. Those organic compounds have different binding strengths with the to-be-detected gas molecule, respectively. The detector is configured by covering the GFET including the organic probe by the chamber.

(Detection of Gas Molecule)

As the to-be-detected gas molecule, dimethyl methylphosphonic acid (DMMP, the molecular weight: 124) is used, which is a noxious and organic phosphorous material. The DMMP as the to-be-detected substance is liquid at room temperature and has the flash point of 69 degrees Celsius and the boiling point of 181 degrees Celsius. Also, the DMMP has the vapor pressure of 79 Pa (at 20 degrees Celsius). The DMMP has a stable property as liquid at room temperature. In order to vaporize this type of liquid, it is common to encourage the vaporization by increasing the temperature. Nevertheless, a more simplified method is employed such as a method of encouraging the vaporization by performing so-called bubbling, which aerates the liquid with an inert gaseous body in order to enhance a surface area of the liquid, or blowing a gaseous body onto the liquid surface or the like. The concentration of the gaseous body obtained in this way is approximately in the order of ppm (parts per million) to ppb (parts per billion). By immixing this with the inert gaseous body, it is possible to further reduce the concentration of the gaseous body.

In the Example 1, the DMMP containing gas with the DMMP concentration of 80 ppb is prepared by use of the blowing method using nitrogen ($N_2$) gas. After inside the chamber, which is provided such that the chamber covers the GFET having the organic probe of the detector, is exhausted by the pump, the DMMP containing gas is introduced inside the chamber. Before and after the introduction of the DMMP containing gas, the drain current when the back gate voltage is swept between −100 to +100 V under the predetermined drain voltage and the time response of the drain current under the predetermined drain voltage and the predetermined back gate voltage are measured. As the recognition result by the six detection cells, the relative signal intensity pattern shown in FIG. 4 is obtained. The detection of the DMMP is determined from the signal intensity pattern shown in FIG. 4.

(Reactivation of Organic Probe)

During the above mentioned detection processing of the gas molecule, it is determined that the whole organic probes have adsorbed the to-be-detected gas molecules by determining that the time response of the drain current does not change any more. After then, inside the chamber is controlled at the atmosphere having the oxygen concentration equal to or less than 1% by exhausting the gas inside the chamber with the pump. Under this kind of condition, the voltage of 4 V is applied for five minutes between the source electrode and the drain electrode to refresh the organic probe.

(Re-Detection of Gas Molecule)

In the detector after the above mentioned reactivation of the organic probe, similarly to the adsorption processing of the gas molecule, the DMMP containing gas, in which the concentration of the DMMP is regulated at 80 ppb by way of the blowing method using the nitrogen ($N_2$) gas, is introduced into the chamber of the detector, which is exhausted by the pump. Before and after the re-introduction of the DMMP containing gas, the drain current when the back gate voltage is swept between −100 to +100 V under the predetermined drain voltage and the time response of the drain current under the predetermined drain voltage and the predetermined back gate voltage are measured. Table 1 shows respective drain current before the gas molecule is adsorbed, after the gas molecule is adsorbed, after the reactivation processing, and after the gas molecule is re-adsorbed.

Example 2

(Preparation of Detector and Detection of Gas Molecule)

Similarly to Example 1, the detection element in which the GFET and the organic probe are combined is prepared. The detector is configured by covering the GFET having the organic probe by the chamber. Subsequently, similarly to Example 1, the DMMP molecule is detected by introducing the DMMP containing gas into the chamber and adsorbing the DMPP molecule with the organic probe. Electric signals are measured before and after the introduction of the DMMP containing gas into the chamber.

(Reactivation of Organic Probe)

During the above mentioned detection processing of the gas molecule, it is determined that the to-be-detected gas molecule is adsorbed with the whole organic probes by determining that the time response of the drain current does not change any more. After then, nitrogen gas having the oxygen concentration equal to or less than 1% is introduced into the chamber, and inside the chamber is controlled at the inert gas atmosphere having the oxygen concentration equal to or less than 1%. Under this kind of condition, the voltage of 4V is applied for five minutes between the source electrode and the drain electrode to refresh the organic probe.

(Re-Detection of Gas Molecule)

In the detector after the above mentioned reactivation of the organic probe, similarly to Example 1, the DMMP containing gas is introduced. Before and after the re-introduction of the DMMP containing gas into the chamber, electric signals are measured. Table 1 shows respective drain current before the gas molecule is adsorbed, after the gas molecule is adsorbed, after the reactivation processing, and after the gas molecule is re-adsorbed.

Comparative Example 1

(Preparation of Detector and Detection of Gas Molecule)

Similarly to Example 1, the detection element in which the GFET and the organic probe are combined is prepared. The detector is configured by covering the GFET having the organic probe by the chamber. Subsequently, similarly to Example 1, the DMMP molecule is detected by introducing the DMMP containing gas into the chamber and adsorbing the DMPP molecule with the organic probe. Electric signals are measured before and after the introduction of the DMMP containing gas into the chamber.

(Re-Detection of Gas Molecule)

During the above mentioned detection processing of the gas molecule, it is determined that the DMMP as the to-be-detected gas molecules are adsorbed with the whole organic probes by determining that the time response of the drain current does not change any more. Subsequently, after the gas inside the chamber is exhausted by the pump, the DMMP containing gas is re-introduced into the chamber. Before and after the re-introduction of the DMMP containing gas into the chamber, electric signals are measured. Table 1 shows respective drain current before the gas molecule is adsorbed, after the gas molecule is adsorbed, after the gas is exhausted, and after the gas molecule is re-adsorbed. Comparative Example 1 only exhausts the gas inside the chamber and does not perform the reactivation processing of the organic probe.

Reference Example 1

(Preparation of Detector and Detection of Gas Molecule)

Similarly to Example 1, the detection element in which the GFET and the organic probe are combined is prepared. The detector is configured by covering the GFET having the organic probe by the chamber. Subsequently, similarly to Example 1, the DMMP molecule is detected by introducing the DMMP containing gas into the chamber and adsorbing the DMPP molecule with the organic probe. Electric signals are measured before and after the introduction of the DMMP containing gas into the chamber.

(Reactivation of Organic Probe)

During the above mentioned detection processing of the gas molecule, it is determined that the DMMP as the to-be-detected gas molecules are adsorbed with the whole organic probe by determining that the time response of the drain current does not change any more. After then, inside the chamber is controlled at atmosphere having the oxygen concentration equal to or less than 1% by exhausting the gas inside the chamber by the pump. Under this kind of condition, the voltage of 3 V is applied for five minutes between the source electrode and the drain electrode.

(Re-Detection of Gas Molecule)

In the detector after the above mentioned reactivation of the organic probe, similarly to Example 1, the DMMP containing gas is introduced. Before and after the re-introduction of the DMMP containing gas inside the chamber, electric signals are measured. Table 1 shows respective drain current before the gas molecule is adsorbed, after the gas molecule is adsorbed, after the reactivation processing, and after the gas molecule is re-adsorbed.

Reference Example 2

(Preparation of Detector and Detection of Gas Molecule)

Similarly to Example 1, the detection element in which the GFET and the organic probe are combined is prepared. The detector is configured by covering the GFET having the organic probe by the chamber. Subsequently, similarly to Example 1, the DMMP molecule is detected by introducing the DMMP containing gas into the chamber and adsorbing the DMPP molecule with the organic probe. Electric signals are measured before and after the introduction of the DMMP containing gas into the chamber.

(Reactivation of Organic Probe)

During the above mentioned detection processing of the gas molecule, it is determined that the DMMP as the to-be-detected gas molecules are adsorbed with the whole organic probe by determining that the time response of the drain current does not change any more. After then, the gas inside the chamber is exhausted and further atmospheric air is introduced into the chamber. Under this kind of condition, the voltage of 4 V is applied for five minutes between the source electrode and the drain electrode.

(Re-Detection of Gas Molecule)

In the detector after the above mentioned reactivation of the organic probe, similarly to Example 1, the DMMP containing gas is introduced. Before and after the re-introduction of the DMMP containing gas into the chamber, electric signals are measured. Table 1 shows respective drain current before the gas molecule is adsorbed, after the gas molecule is adsorbed, after the reactivation processing, and after the gas molecule is re-adsorbed.

Reference Example 3

(Preparation of Detector and Detection of Gas Molecule)

Similarly to Example 1, the detection element in which the GFET and the organic probe are combined is prepared. The detector is configured by covering the GFET having the organic probe by the chamber. Subsequently, similarly to Example 1, the DMMP molecule is detected by introducing the DMMP containing gas into the chamber and adsorbing the DMPP molecule with the organic probe. Electric signals are measured before and after the introduction of the DMMP containing gas into the chamber.

(Reactivation of Organic Probe)

During the above mentioned detection processing of the gas molecule, it is determined that the DMMPs as the to-be-detected gas molecules are adsorbed with the whole organic probe by determining that the time response of the drain current does not change any more. After then, the nitrogen gas having the oxygen concentration of 2% is introduced into the chamber, and inside the chamber is controlled at the gas atmosphere having the oxygen concentration of 2%. Under this kind of condition, the voltage of 4 V is applied for five minutes between the source electrode and the drain electrode.

(Re-Detection of Gas Molecule)

In the detector after the above mentioned reactivation of the organic probe, similarly to Example 1, the DMMP containing gas is introduced. Before and after the re-introduction of the DMMP containing gas into the chamber, electric signals are measured. Table 1 shows respective drain current before the gas molecule is adsorbed, after the gas molecule is adsorbed, after the reactivation processing, and after the gas molecule is re-adsorbed.

TABLE 1

| | Drain Current at Back Gate Voltage of 20 V [μA] | | | |
| --- | --- | --- | --- | --- |
| | Before Adsorpotion | After Adsorption | After Reactivation | After Re-adsorption |
| Example 1 | 61.9 | 67.0 | 61.7 | 66.9 |
| Example 2 | 58.5 | 64.7 | 58.4 | 64.4 |
| Comparative Example 1 | 61.5 | 66.8 | (66.9) | 66.9 |
| Referential Example 1 | 61.3 | 66.6 | 66.7 | 66.7 |
| Referential Example 2 | 52.8 | 58.2 | unmeasurable | unmeasurable |
| Referential Example 3 | 60.1 | 66.9 | unmeasurable | unmeasurable |

As apparent from the result shown in Table 1, in the Example 1 and Example 2, when the oxygen partial pressure inside the atmospheric controlled chamber of the detector is equal to or less than 1%, the sufficient Joule heat can be generated for desorbing the gas molecule from the organic probe by applying the drain voltage equal to or greater than 4 V for five minutes or more. It is determined that the to-be-detected gas molecule is desorbed from the organic probe. Furthermore, it is also confirmed that the organic probe can be refreshed without damaging the graphene layer as the channel or the organic probe, because the organic probe, which has been refreshed, is capable of adsorbing the gas molecule again. As a result, it is turned out that the measurement of the to-be-detected gas molecule can be repetitively performed.

On the other hand, in Comparative Example 1, the drain current does not present changes before and after the gas exhaustion inside the chamber. For this reason, it is turned out that the organic probe is maintained in a state that the to-be-detected gas molecule is being adsorbed with the organic probe and the to-be-detected gas molecule cannot be re-detected. Furthermore, it is turned out that the sufficient Joule heat is not generated for desorbing the gas molecule from the organic probe and the to-be-detected gas molecular cannot be desorbed, because the drain current does not present changes before and after the reactivation processing by applying the drain voltage of 3 V in Reference Example 1. Under the condition in Reference Example 2 and Reference Example 3, as the oxygen partial pressure inside the chamber is higher, the Joule heat generated during the reactivation processing causes the graphene to be oxidized and damaged, and the graphene film does not function as the channel of the FET any more so that the electric signals cannot be obtained. According to the above results, it is preferable to control inside the chamber of the detector at atmosphere having the oxygen concentration equal to or less than 1% and to apply the drain voltage of 4 V for five minutes or more in order to configure the gas detection apparatus that is capable of measuring repetitively.

While certain embodiments of the present invention have been described, these embodiments have been presented by way of example only, and are not intended to limit the scope of the invention. Indeed, the novel embodiments described herein may be embodied in a variety of other forms. Various omissions, substitutions, changes and modifications may be made to the embodiments described herein without departing from the spirit and scope of the present invention. The appended claims and their equivalents are intended to cover such embodiments and modifications as would fall within the scope and spirit of the invention.

What is claimed is:

1. A gas detection apparatus, comprising:
   a collection unit collecting detection target gas containing gas molecules to be detected;
   a detector including a plurality of detection cells each having a sensor unit and an organic probe disposed at the sensor unit, the organic probe capturing the gas molecules collected by the collection unit;
   a discriminator discriminating the gas molecules by a signal pattern based on an intensity difference of detection signals generated with the gas molecules being captured by the organic probes of the plurality of detection cells; and
   a reactivation unit applying heat to the organic probes which have the captured gas molecules to be desorbed the gas molecules from the organic probes.

2. The gas detection apparatus of claim 1, wherein the sensor unit comprises a field effect transistor including a graphene layer and a source electrode and a drain electrode both connected to the graphene layer, and the organic probe is provided on the graphene layer.

3. The gas detection apparatus of claim 2, wherein the reactivation unit comprises a circuit applying voltage or current between the source electrode and the drain electrode when the organic probe is regenerated, to generate Joule heat in the graphene layer so as to heat the organic probe.

4. The gas detection apparatus of claim 3, wherein the reactivation unit generates the Joule heat to the graphene layers of the plurality of detection cells under conditions corresponding to the organic probes of the plurality of detection cells, respectively.

5. The gas detection apparatus of claim 1, wherein the reactivation unit applies heat to the organic probe such that a temperature of the organic probe is equal to or higher than a temperature for desorbing the gas molecule and less than an oxidation temperature or a decomposition temperature of the graphene layer.

6. The gas detection apparatus of claim 1, wherein the plurality of detection cells have a plurality of the organic probes having different binding strength with the gas molecule one another.

7. The gas detection apparatus of claim 1, wherein the plurality of detection cells are covered with a chamber which has a gas introducing tube and a gas exhaust tube and is capable of controlling atmosphere.

8. The gas detection apparatus of claim 7, wherein the gas introducing tube includes a first gas introducing tube introducing the detection target gas into the chamber and a second gas introducing tube introducing an inert gas having oxygen content of 1% by volume or less when the organic probe is regenerated.

9. The gas detection apparatus of claim 1, wherein the gas molecule is a compound molecule containing phosphorus.

\* \* \* \* \*